United States Patent
Wang et al.

(10) Patent No.: US 11,584,699 B2
(45) Date of Patent: Feb. 21, 2023

(54) PROCESSES TO CONVERT PARAFFINS TO HEAVIER PRODUCTS

(71) Applicant: ExxonMobil Technology and Engineering Company, Annandale, NJ (US)

(72) Inventors: Kun Wang, Branchburg, NJ (US); David O. Marler, Easton, PA (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/086,567

(22) Filed: Nov. 2, 2020

(65) Prior Publication Data

US 2021/0188738 A1  Jun. 24, 2021

Related U.S. Application Data

(60) Provisional application No. 62/950,235, filed on Dec. 19, 2019.

(51) Int. Cl.
*C07C 2/76* (2006.01)

(52) U.S. Cl.
CPC ............ *C07C 2/76* (2013.01); *C07C 2521/06* (2013.01); *C07C 2523/42* (2013.01)

(58) Field of Classification Search
CPC .................. C07C 7/26; C07C 2521/06; C07C 2523/42; C07C 2601/14; C07C 2/80
See application file for complete search history.

(56) References Cited

U.S. PATENT DOCUMENTS

| | | | | |
|---|---|---|---|---|
| 3,451,909 A | * | 6/1969 | Chloupekfrank | ......... C07C 2/58 204/157.15 |
| 2016/0200586 A1 | * | 7/2016 | Forsyth | ................ C01C 3/0212 423/376 |
| 2019/0120029 A1 | * | 4/2019 | Knight | .................... E21B 43/18 |
| 2019/0284481 A1 | * | 9/2019 | Hu | ........................... B01J 37/08 |

OTHER PUBLICATIONS

S.H. Brown, "Making mercury-photosensitized dehydrodimerization into an organic synthesis method: vapor pressure selectivity and the behavior of functionalized substrates" J. Am. Chem. Soc., 1989, 111, pp. 2935-2946, New Haven, Connecticut.

D. Ravelli, "Decatungstate anion for photocatalyzed 'window ledge' reactions" Acc. Chem. Res., 2016, vol. 49, pp. 2232-2242, Pavia, Italy.

A. Hainer, "Highly electrophilic titania hole as a versatile and efficient photochemical free radical source" J. Am. Chem. Soc., 2019, vol. 141, pp. 4531-4535, Canada.

A. Yamamoto, "Visible-light-induced photocatalytic benzene/cyclohexane cross-coupling utilizing a ligand-to-metal charge transfer benzene complex adsorbed on titanium oxides" Cat. Sci. Tech., 2018, vol. 8, pp. 2046-2050.

* cited by examiner

*Primary Examiner* — Thuan D Dang

(74) *Attorney, Agent, or Firm* — Shook, Hardy & Bacon L.L.P.

(57) ABSTRACT

The present disclosure generally relates to a process for converting a hydrocarbon feed including introducing a hydrocarbon feed comprising a $C_{1+}$ alkane to a catalyst composition in a reactor, the catalyst composition comprising a Group 6-Group 15 metal supported on a support; and irradiating the hydrocarbon feed and the catalyst composition with electromagnetic energy in the reactor at reactor conditions to produce a product comprising a $C_{2+}$ alkane, wherein the $C_{2+}$ alkane of the product is heavier than the $C_{1+}$ alkane in the hydrocarbon feed.

12 Claims, 1 Drawing Sheet

PROCESSES TO CONVERT PARAFFINS TO HEAVIER PRODUCTS

FIELD

The present disclosure generally relates to processes to upgrade hydrocarbon feeds, and more particularly to conversion of light paraffins to heavier hydrocarbons such as gasoline and/or distillate products in the presence of catalyst compositions and electromagnetic energy.

BACKGROUND

As the production of shale and tight oils is increasing in the United States, light paraffins ($C_2$-$C_9$) such as liquefied petroleum gas (LPG, e.g., $C_3$/$C_4$) and natural gasoline (e.g., $C_5$-$C_6$) are becoming more abundant and at lower costs. At the same time, demand for light paraffins is decreasing, particularly with the growth of high performance, more efficient gasoline engines which typically require higher octane gasoline. This imbalance of supply and demand is likely to become worse with time. Upgrading light paraffins to higher value products, although desirable, remains challenging.

Conversion of light paraffins to heavier hydrocarbon products, such as chemicals and distillate fuels (e.g., jet fuel and diesel fuel), provides a high value outlet for the supply of light paraffins. However, conventional upgrading processes to convert light paraffins to distillate typically require high amounts of energy consumption. For example, a process to upgrade light paraffins could include steam cracking or catalytic dehydrogenation of paraffins to generate olefins, followed by olefin chemistries such as oligomerization, polymerization and alkylation; or converting the feed to syngas via partial oxidation, followed by Fischer-Tropsch or methanol to hydrocarbons synthesis. These approaches involve high temperatures, such as temperatures greater than 400° C., and are energy intensive. Other processes to upgrade alkanes include using electromagnetic energy. However, such processes often have low coupling efficiencies, poor safety/health/environment concerns (S/H/E) due to the use of materials such as mercury and UV-C exposure, and/or slow reaction times.

There is a need for new and improved processes to convert light paraffins to, e.g., gasoline and/or distillate using less energy-intensive processes.

SUMMARY

In an embodiment is provided a process for converting a hydrocarbon feed that includes introducing a hydrocarbon feed comprising a $C_{1+}$ alkane to a catalyst composition in a reactor, the catalyst composition comprising a Group 6-Group 15 metal supported on a support; and irradiating the hydrocarbon feed and the catalyst composition with electromagnetic energy in the reactor at reactor conditions to produce a product comprising a $C_{2+}$ alkane, wherein the $C_{2+}$ alkane of the product is heavier than the alkane in the hydrocarbon feed.

In another embodiment is provided a process for converting a hydrocarbon feed that includes introducing a hydrocarbon feed comprising a alkane to a catalyst composition in a reactor, the catalyst composition comprising a Group 6-Group 15 metal supported on a support; and irradiating the hydrocarbon feed and the catalyst composition with electromagnetic energy in the reactor at reactor conditions to produce a product comprising a $C_{2+}$ alkene.

In another embodiment is provided a process for converting a hydrocarbon feed that includes introducing a hydrocarbon feed comprising a $C_2$-$C_{12}$ alkane to a catalyst composition in a reactor, the catalyst composition comprising a Group 10 metal supported on an oxide support; and irradiating the hydrocarbon feed and the catalyst composition with UV-A radiation in the reactor at reactor conditions to produce a product comprising a $C_4$-$C_{24}$ alkane, wherein the $C_4$-$C_{24}$ alkane of the product is heavier than the $C_2$-$C_{12}$ alkane in the hydrocarbon feed.

DETAILED DESCRIPTION

Figure 1:
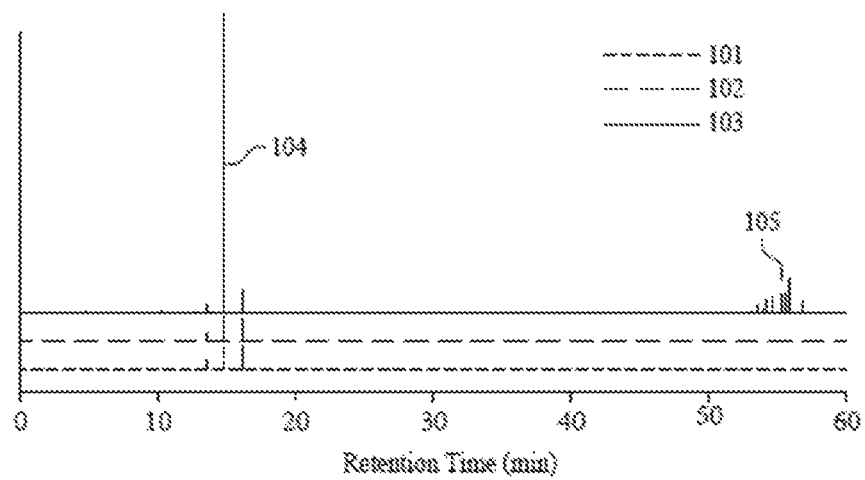
FIG. 1 depicts a gas chromatography (GC) trace of n-heptane, a GC trace of a comparative n-heptane irradiated with UV-A light in the presence of $TiO_2$, and a GC trace of an example n-heptane irradiated with UV-A light in the presence of $Pt/TiO_2$, according to at least one embodiment of the present disclosure.

The present disclosure generally provides processes to upgrade hydrocarbon feeds, and more particularly to conversion of paraffins to heavier hydrocarbons such as gasoline and/or distillate products in the presence of catalyst compositions and electromagnetic energy. In contrast to conventional methods, the processes described herein can occur at ambient temperature and/or pressure. The inventors have discovered new and improved processes that, at least, unexpectedly increase the selectivity to produce heavier hydrocarbons. The inventors surprisingly found that, at least, the processes described herein enable upgrading hydrocarbon feeds with commercially useful reaction times, such as less than about 24 hours, without the use of materials that compromise safety/health/environment (S/H/E) considerations. Further, the inventors have discovered a process that is, at least, less energy intensive than traditional thermal methods of upgrading hydrocarbon feeds.

For purposes of this disclosure, and unless otherwise indicated, a "composition" includes components of the composition and/or reaction products of two or more components of the composition.

For purposes of this disclosure, and unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

For purposes of this disclosure, and unless otherwise indicated, the article "a" or "an" shall refer to "at least one" unless specified to the contrary or the context clearly indicates otherwise. Thus, embodiments comprising "an alkane" include embodiments comprising one, two, or more alkanes, unless specified to the contrary or the context clearly indicates only one alkane is included.

For purposes of this disclosure, and unless otherwise indicated, an "olefin," alternatively referred to as "alkene," is a linear, branched, or cyclic compound of carbon and hydrogen having at least one double bond.

As used herein, and unless otherwise specified, the term "$C_n$," means hydrocarbon(s) having n carbon atom(s) per molecule, wherein n is a positive integer. The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Likewise, a "$C_m$-$C_y$," group or compound refers to a group or compound comprising carbon atoms at a total number thereof in the range from m to y. Thus, a $C_1$-$C_{50}$ alkyl group refers to an alkyl group comprising carbon atoms at a total number thereof in the range from 1 to 50.

For purposes of this disclosure, and unless otherwise indicated, the term "acyclic alkane" includes linear and branched acyclic alkanes.

For the purposes of this disclosure, the term "photocatalyst," includes materials that absorb light and generate reactive centers to cause or to promote a chemical reaction to occur.

For purposes of this present disclosure and the claims thereto, the nomenclature of Periodic Table of Elements and the Periodic Table Groups is used as described in CHEMICAL AND ENGINEERING NEWS, 63(5), pg. 27 (1985). Abbreviations for atoms are as given in the periodic table (Si=silicon, for example). For example, a "group 10 metal" is an element from group 10 of the Periodic Table, e.g. Ni, Pd, or Pt.

Catalyst Composition

In at least one embodiment, the present disclosure relates to a catalyst composition, e.g., a photocatalyst composition, that includes a semiconductor component and a metal nanoparticle component. In some embodiments, the catalyst can include an non-reactive binder such as alumina or silica. The non-reactive binder may act as an aid to shape the catalyst into bodies suitable for use in a photo-reactor. In at least one embodiment, the catalyst can be spray-dried into spherical particles by suitable methods known in the art. In some embodiments, a catalyst powder can be formed by suitable methods known in the art and coated on a surface such as a flat surface of the reactor or on a monolith structure, such as a foam structure, by suitable methods known in the art. For example, the monolith or foam can be ceramic, glassy, or metallic. In some embodiments, the monolith or foam may substantially absorb the electromagnetic energy. In some embodiments, the monolith or foam may not substantially absorb the electromagnetic energy. In some embodiments, the catalyst composition is formed into or onto a foam or monolith structure. In some embodiments, the base surface is non-reactive and does not absorb electromagnetic energy when exposed to electromagnetic energy. For example, the non-reactive surface can be quartz or borosilicate glass.

In some embodiments, the semiconductor component can be a material with a band gap that corresponds to the energy range for the electromagnetic energy source used for a photocatalytic reaction. By way of example, $TiO_2$ has a band gap of 3.2 eV (corresponding to an electromagnetic energy with λ=387 nm) and can be activated with UV light radiation with wavelengths of about 387 nm or less, for example, UV-C (about 100 to about 280 nm), UV-B (about 280 to about 315 nm), or UV-A (about 315 to about 380 nm).

The term "band gap," as used herein, is the energy difference between the valence band ("VB") of electrons and the conduction band ("CB"). Table 1 depicts the valence band and the conductive band potentials versus Normal Hydrogen Electrode (NHE) at pH 7 and band gap energies for different semiconductors that can be useful for the present the disclosure. The table is adapted from Schreck, "Photocatalytic Gas Phase Reactions." Chem. Mat., 2019, 31, 597-618, which is incorporated herein in its entirety.

TABLE 1

VB and CB versus the NHE at pH 7 and Band Gap Energies for Semiconductors

| Semiconductor | Conductive Band Edge (V) | Valence Band Edge (V) | Band Gap Energy (eV) |
| --- | --- | --- | --- |
| $Fe_2O_3$ | −0.2 V | +1.9 V | 2.1 eV |
| $WO_3$ | −0.3 V | +2.3 V | 2.6 eV |
| $TiO_2$ | −0.5 V | +2.7 V | 3.2 eV |
| Si | −0.8 V | 0.3 V | 1.1 eV |
| $Cu_2O$ | −1.3 V to −1.2 V | 0.7 V to 0.8 V | 2.0 eV to 2.2 eV |
| TaON | −0.8 V to −0.7 V | 1.7 V | 2.4 eV |
| CdSe | −0.1 V | 1.6 V | 1.7 eV |
| ZnO | −0.5 V | 2.8 V | 3.3 eV |
| $SnO_2$ | −0.1 V | 3.5 V | 3.6 eV |
| CdS | −0.6 V | 1.7 V | 2.4 eV |
| $LiTaO_2$ | −1.7 V | 3.1 V | 4.8 eV |
| $NaTaO_2$ | −1.5 V | 2.5 V | 4.0 eV |
| $KTaO_2$ | −1.3 V | 2.3 V | 3.6 eV |
| $NaNbO_3$ | −7 V | 2.6 V | 3.3 eV |
| $KNbO_3$ | −0.6 V | 2.5 V | 3.1 eV |
| $CaTiO_3$ | −1.3 V | 2.2 V | 3.5 eV |
| $SrTiO_3$ | −1.3 V | 1.9 V | 3.2 eV |
| $PbTiO_3$ | −0.7 V | 2.2 V | 2.9 eV |
| $BaZrO_3$ | −1.8 V | 3.0 V | 4.8 eV |
| $BaCeO_3$ | −1.5 V | 1.7 V | 3.2 eV |
| $LaFeO_3$ | 0.2 V | 1.8 V | 2.0 eV |
| $CaTaO_2N$ | −1.7 V | 0.9 V | 2.6 eV |
| $SrTaO_2N$ | −1.0 V | 1.1 V | 2.1 eV |
| $BaTaO_2N$ | −0.9 V | 1.1 V | 2.0 eV |
| $Bi_2WO_6$ | −0.7 V | 2.0 V | 2.7 eV |
| $La_2Ti_2O_7$ | −0.7 V | 3.3 V | 4.0 eV |

During a photoexcitation process, a charge separation can occur in which a photon with an energy equal to or higher than that of the band gap is absorbed, and an electron is excited from the VB to the CB causing a hole to be left in the VB. The charge carriers (i.e., electrons and holes) can then migrate to the surface of a catalyst particle of the catalyst composition and can transfer to a surface-adsorbed reactant (e.g., a hydrocarbon reactant), participating in the redox reaction. As used herein, the term "redox" refers to the transfer of electrons between chemical species. Example Mechanism 1, provided below, shows an example mechanism of a redox reaction that occurs at the surface of a catalyst particle of an example catalyst composition ($MO_2$) in the presence of electromagnetic energy and/or radiation (hv) used for a photocatalytic reaction. As shown in Example Mechanism 1, it is believed that the photoexcited electrons ($e^-$) reduce $O_2$, and the holes ($h^+$) oxidize the electron acceptor (OH—) (equations 1-5). In the presence of a hydrocarbon, the charge carriers can then promote a reaction such as alkane dehydrogenation and dehydrogenative coupling. However, it is also possible for the electrons and holes to recombine (equation 6), resulting in heat, within the bulk of the semiconductor component or the surface of the semiconductor component which can prevent or minimize any redox processes. The recombination is an inefficiency that is often faced when using of semiconductors.

Example Mechanism 1

$$MO_2 + h\nu \rightarrow h^+ + e^- \quad (1)$$

$$O_2 + e^- \rightarrow O_2^{.-} \quad (2)$$

$$O_2^{.-} + O_2^{.-} + 2H^+ \rightarrow H_2O_2 + O_2 \quad (3)$$

$$O_2^{.-} + h^+ \rightarrow O_2 \quad (4)$$

$$OH^- + h^+ \rightarrow HO. \quad (5)$$

$$e^- + h^+ \rightarrow \text{recombination (heat)} \quad (6)$$

wherein $MO_2$ represents an example catalyst composition; hv represents electromagnetic energy and/or radiation; $h^+$ represents a hole; and $e^-$ represents an electron.

By way of example, in order for reduction and oxidation steps to occur in the Example Mechanism 1, the reduction or oxidation potential (V) should lie from the CB edge to the VB edge of the semiconductor such as the CB edge and the VB edge listed in Table 1.

The inventors have found that, at least, depositing a metal nanoparticle to the semiconductor can reduce inefficiencies with semiconductors used for dehydrogenation and dehydrogenative coupling. The addition of the metal nanoparticle having a Fermi level that corresponds to the conduction band of the semiconductor can enable the flow of the photoexcited electrons from the semiconductor to the metal nanoparticle which can decrease the tendency for the electrons to recombine with the holes. The Fermi level is the highest energy state ($E_F$) occupied by electrons in a material at absolute zero temperature. The Fermi level can be determined by the work function ($\Phi$), which corresponds to the minimum amount of energy needed to remove an electron from the metal (from $E_F$ to the vacuum level). The electron work function for the elements can be found in the "*CRC Handbook of Chemistry and Physics*" (David R. Lide, Editor-in-Chief, $82^{nd}$ Edition, 2001-2002; page 12-130), which is incorporated herein by reference in its entirety. For example, the work function for polycrystalline Pt is 5.64 eV, polycrystalline Pd is 5.22 eV, polycrystalline Rh is 4.98 eV, and polycrystalline Ru is 4.71 eV. Without being bound by theory, it is believed that the added metal nanoparticles can act as electron receivers and can also participate in the reaction as a co-catalyst resulting in improved product yield. For example, instead of an electron recombining with a hole in the valence band, the electron can be received by the metal nanoparticle at conductive band.

As a non-limiting example, Example Mechanism 2 shows an example catalytic alkane dehydrogenation and dehydrogenative coupling of propane. As can be seen in equation 7, the metal nanoparticle component of the catalyst composition ($M_1$) receives photoexcited electrons ($e^-$). In equation 8, the holes oxidize the propane molecules to generate propyl radicals and protons. The propyl radicals can then couple to form longer hydrocarbons (equation 10), and/or form propylene and propane as products (equation 9). Finally, the protons generated in equation 8 can then be reduced by the photoexcited electron to produce hydrogen on the surface of the metal nanoparticle component of the catalyst composition ($M_1$) (equation 11).

Example Mechanism 2

$$M_1/M_2O_x + h\nu \rightarrow M_2O_x(h^+) + M_1(e^-) \quad (7)$$

$$C_3H_8 + M_2O_x(h^+) \rightarrow M_2O_x + C_3H_7 + H^+ \quad (8)$$

$$2.C_3H_7 \rightarrow C_3H_6 + C_3H_8 \quad (9)$$

$$2.C_3H_7 \rightarrow C_6H_{14} \quad (10)$$

$$2H^+ + 2M_1(e^-) \rightarrow 2M_1 + H_2 \quad (11)$$

wherein $M_1/M_2O_x$ represents an example catalyst composition; $M_1$ represents an example metal nanoparticle component of the catalyst; $M_2O_x$ represents an example semiconductor component of the catalyst composition; hv represents electromagnetic energy; $h^+$ represents a hole; and $e^-$ represents an electron.

In addition to acyclic alkanes, the processes and catalyst compositions of the present disclosure can also generate carbon-centered radicals from cycloalkanes by breaking $sp^3$ C—H bonds. For example, the $sp^3$ C—H bonds in cyclohexane have a bond strength of 95.5 kcal/mol. The bond strength of secondary C—H bonds in acyclic alkanes are comparable to $sp^3$ C—H bonds of cycloalkanes. For example, the secondary C—H bond in n-butane is about 96.4 kcal/mol. Thus, the inventors have found that catalyst compositions of the present disclosure can break certain C—H bonds in paraffins such as secondary C—H bonds in acyclic alkanes and $sp^3$ C—H bonds of cycloalkanes, generating carbon-centered (alkyl) radicals which can disproportionate to form olefins/paraffins or couple to form paraffins. By way of example, $sp^3$ C—H for cyclohexane can be broken, generating carbon-centered radicals that can then homocouple to form bicyclohexyl. An additional benefit to performing the process under low energy conditions, such as ambient conditions, is that the alkyl radicals are less likely to undergo scission forming lighter hydrocarbons.

The inventors have found that the catalyst compositions described herein can be used as an alternative to thermal catalysis for paraffin dehydrogenation to form olefins and/or dehydrogenative coupling to form heavier alkanes. Thermal catalysis at high temperatures are typically used because paraffin dehydrogenation and dehydrogenative coupling reactions are not thermodynamically favored at ambient conditions. At 1 atmosphere pressure (14.7 psig), the free energy for propane dehydrogenation is negative only at temperatures higher than about 600° C.; and the free energy for paraffin dehydrogenative coupling is positive and unfavored even at temperatures above 1000° C. In contrast to traditional methods, the catalyst compositions and methods described herein can be used at lower temperatures such as ambient conditions.

In some embodiments, the semiconductor component is an oxide compound, a perovskite, a sulfide, a metal, a metal alloy, or a combination thereof. The semiconductor component can have a band gap in the range of from about 2 to about 4 eV, such as from about 2.5 to about 3.5 eV. In some embodiments, the semiconductor component can be selected from the group consisting of $Fe_2O_3$, $WO_3$, $MoO_3$, $TiO_2$, Si, $Cu_2O$, TaON, CdSe, ZnO, $SnO_2$, $Bi_2O_3$, $BiVO_4$, $MoS_2$, CdS, $LiTaO_3$, $NaTaO_3$, $KTaO_3$, $NaNbO_3$, $KNbO_3$, $CaTiO_3$, $SrTiO_3$, $PbTiO_3$, $BaZrO_3$, $BaCeO_3$, $LaFeO_3$, $CaTaO_2$, $SrTaO_2N$, $BaTaO_2N$, $Bi_2WO_6$, $La_2Ti_2O_7$, and a combination thereof. In some embodiments, the semiconductor component can be selected from the group consisting of $TiO_2$, ZnO, $NaNbO_3$, $KNbO_3$, $SrTiO_3$, $PbTiO_3$, $BaCeO_3$, $Bi_2O_3$, $BiVO_4$, $MoS_2$, and a combination thereof.

In some embodiments, the metal nanoparticle component is a Periodic Table Group 6, 7, 8, 9, 10, 11, 12, 13, 14, and/or 15 metal, such as a Group 8, 9, 10, 11, 12, and/or such as a Group 8, 9, 10, and/or 11 metal, such as a Group 10 metal. By way of example, the metal nanoparticle component can include one or more of Pt, Pd, Ni, Co, Fe, Rh, Ir, Au, Ag, Cu, Ru, Bi, Sn, Zn, Ga, or a mixture thereof, such as binary and ternary mixtures thereof. In at least one embodiment, the metal nanoparticle component can be selected to correspond to the metal Fermi level of the conduction band of the semiconductor. For example, the catalyst composition can be Pt/TiO$_2$ (anatase), Pd/TiO$_2$ (anatase). In some embodiments, the metal nanoparticle component can be selected based on the predetermined selectivity of the hydrocarbon product. For example, the metal nanoparticle component can be selected to produce a higher yield of heterocoupled product. Alternatively or additionally, the metal nanoparticle component can be selected to produce a higher yield of homocoupled product. Alternatively or additionally, the metal nanoparticle component can be selected to produce a higher yield of heavy alkanes and a lower yield of alkenes.

In some embodiments, the metal nanoparticle component can be free or substantially free of one or more Group 12 metals. In some embodiments, the metal nanoparticle component is free or substantially free of mercury. The inventors have found that a Group 6 to Group 15, such as a Group 8 to Group 11 metal can be used for the processes of the present disclosure, greatly reducing the carbon footprint and minimizing other safety, health, and environmental (S/H/E) challenges for paraffin upgrading.

Example catalyst compositions suitable for alkane dehydrogenation and dehydrogenative coupling can include metal nanoparticles supported on the semiconductor component. The metal nanoparticle component of the catalyst composition can range from about 0.05 wt % to about 50 wt % of the catalyst composition, such as from about 0.1 wt % to about 5 wt %, such as from about 0.2 wt % to about 2 wt %, such as about 1 wt %, by total weight of the catalyst composition. In some embodiments, the catalyst composition can be in the form of a powder or spherical particles suspended in solution. In some embodiments, the catalyst composition can be in the form of a thin film coated on an illuminated reactor surface. In some embodiments, the catalyst composition has a particle size of about 1 to about 100,000 nm (~100 micron), such as about 2 nm to about 10,000 nm (~10 micron), such as from about 5 nm to about 1,000 nm (~1 micron), such as from about 10 nm to about 100 nm. In some embodiments the catalyst composition has a total surface area of from about 5 m$^2$/g to about 500 m$^2$/g, such as from about 10 m$^2$/g to about 400 m$^2$/g, such as from about 100 m$^2$/g to about 200 m$^2$/g as determined by Brunauer, Emmet and Teller (BET) method.

For purposes herein, the surface area (SA, also called the specific surface area or BET surface area), pore volume (PV), and pore diameter (PD) of catalyst support materials are determined by the BET method and/or Barrett-Joyner-Halenda (BJH) method using adsorption-desorption of nitrogen (temperature of liquid nitrogen: 77 K) with a MICROMERITICS TRISTAR II 3020 instrument or MICROMERITICS ASAP 2420 instrument after degassing of the powders for 4 to 8 hours at 100 to 300° C. or 4 hours to overnight at 40° C. to 100° C. More information regarding the method can be found, for example, in "Characterization of Porous Solids and Powders: Surface Area, Pore Size and Density," S. Lowell et al., Springer, 2004. PV refers to the total PV, including both internal and external PV. For purposes of the claims, the BET method is used to determine the surface area.

The semiconductor component of the catalyst composition can range from about 50 wt % to about 99.95 wt % of the catalyst composition, such as from about 95 wt % to about 99.9 wt %, such as from about 98 wt % to about 99.8 wt %, such as about 99 wt %, by total weight of the catalyst composition.

In at least one embodiment, the catalyst composition is Pt and/or Pd supported on a support such as TiO$_2$.

Reaction and Process Conditions

Processes to convert a hydrocarbon feed can further include irradiating the hydrocarbon feed and catalyst composition with electromagnetic energy in the reactor at reactor conditions to produce a hydrocarbon product. In some embodiments, electromagnetic energy is supplied to the reactor, such as by irradiating the hydrocarbon feed and catalyst composition. In some embodiments, the catalyst composition is shaped into a foam or monolith structure and electromagnetic energy can be supplied to the reactor internally such as by fiber optics or distributed by laser to the channels or pores of the catalyst composition. By way of example, the catalyst composition is coated on an non-reactive monolith structure having a cylindrical shape to form a shaped catalyst composition. The shaped catalyst composition can have channels along the longitudinal direction and the fiber optics can be distributed through the channels and direct electromagnetic energy to the shaped catalyst composition internally. Without being bound by theory, running fiber optics in the shaped catalyst composition internally can increase the surface area of the catalyst composition that is exposed to electromagnetic energy and improve reaction time and product yield. In some embodiments, the catalyst composition can be coated on an non-reactive surface such as a flat or curved non-reactive surface of the reactor wall that does not absorb the electromagnetic energy and the electromagnetic energy can be supplied externally by irradiating from the outer surface of the reactor wall. A number of sources of electromagnetic energy, such as a light source, can be used. By way of example, the light source can be visible light with a wavelength of about 400 to about 600 nm, such as blue light, such as green light. In some embodiments, the light source is a UV-A lamp, laser, and/or a light-emitting diode (LED). In some embodiments, the electromagnetic energy is produced by a light source and/or have a wavelength of greater than about 300 nm, such as from about 300 to about 950 nm, such as from about 350 nm to about 400 nm, alternatively from about 600 nm to about 950 nm. In some embodiments, the reactor can be made from a material capable of illuminating light externally through the reactor surface. For example, the reaction is carried out in a pyrex (borosilicate) or quartz reactor. In some embodiments, the light source is encased in a pyrex (borosilicate) or quartz material, such as through a tube installed in the interior surface of a stirred tank reactor. In some embodiments, the reaction can be performed continuously in a re-circulating reactor (flow or semi-batch) where the product is removed by distillation. In some embodiments, the hydrocarbon feed and the catalyst composition are irradiated for about 24 hours or less, such as from about 0.1 to about 24 hours, such as about 0.5 to about 12 hours, such as from about 5 hours to about 10 hours, alternatively from about 10 to about 20 hours, such as from about 12 to about 18 hours.

In at least one embodiment, a process of the present disclosure includes introducing a hydrocarbon feed that includes one or more alkanes to a catalyst composition in a reactor. In some embodiments, the one or more $C_{1+}$ alkanes is a $C_1$-$C_{50}$ alkane, such as a $C_2$-$C_{20}$ alkane, such as a $C_2$-$C_9$ alkane, such as a $C_2$-$C_5$ alkane. In some embodiments, the one or more $C_{1+}$ alkanes can include an acyclic alkane, such as a $C_1$-$C_{50}$ acyclic alkane, such as a $C_2$-$C_{20}$ acyclic alkane, such as a $C_2$-$C_{12}$ acyclic alkane. The $C_{1+}$ alkane can be a linear alkane or a branched alkane. Examples of $C_1$-$C_{50}$ acyclic alkanes can include methane, ethane, propane, butane, pentane, hexane, heptane, octane, nonane, decane, undecane, dodecane, or a combination thereof. In some embodiments, the one or more $C_{1+}$ alkanes can include a cyclic alkane such as a $C_3$-$C_{50}$ cyclic alkane, such as a such as a $C_3$-$C_{20}$ alkane, $C_3$-$C_{12}$ cyclic alkane. Examples of $C_3$-$C_{50}$ cyclic alkanes can be cyclopropane, cyclobutane, cyclopentane, cyclohexane, cycloheptane, cyclooctane, an isomer thereof, either unsubstituted or substituted with alkyl groups such as methyl, ethyl, propyl, butyl, or a combination thereof.

In some embodiments, the hydrocarbon feed is free or substantially free of functionalized hydrocarbons. As used herein, a "functionalized hydrocarbon" are any hydrocarbons attached to a functional group such as —$NR_2$, —$OR^*$, —SeR, —$TeR^*$, —$PR^*_2$, —$AsR^*_2$, —$SbR^*_2$, —$SR^*$, —$BR_2$, —$SiR^*_3$, —$GeR^*_3$, —$SnR^*_3$, —$PbR^*_3$, where each $R^*$ is independently a hydrocarbyl or halocarbyl radical, and two or more $R^*$ may join together to form a substituted or unsubstituted completely saturated, partially unsaturated, or aromatic cyclic or polycyclic ring structure), or where at least one heteroatom has been inserted within a hydrocarbyl ring. In some embodiments, the hydrocarbon feed can include about 5 mol % or less of functionalized hydrocarbons, such as about 4 mol % or less, such as about 3 mol % or less, such as about 2 mol % or less, such as about 1 mol % or less, based on total mole percent of the hydrocarbon feed as determined by gas chromatography. In some embodiments, the feed may include water. An amount of water in the feed can be from about 1 ppm to about 100000 ppm water, such as from about 5 ppm to about 10000 ppm, such as from about 10 ppm to about 1000 ppm as determined by the Karl Fischer method. Without being bound by theory, it is believed that water in the hydrocarbon feed can improve product yield because the water can generate hydroxyl radicals that can act as an additive or promoter to the reaction by picking up hydrogen.

In some embodiments, the hydrocarbon feed can include less than about 5 mol % alkenes, such as about 4 mol % or less, such as about 3 mol % or less, such as about 2 mol % or less, such as about 1 mol % or less, based on total mole percent of the hydrocarbon feed as determined by gas chromatography. For example, the hydrocarbon feed can include ethylene, propylene, butene, pentene, n-hexene, n-heptene, octene, nonene, decene, undecene, dodecene, cyclopentene, cyclohexene, methylcyclohexene, methylcyclopentene, and their isomers or a mixture thereof.

In at least one embodiment, the hydrocarbon feed composition can be controlled by introducing a predetermined amount of hydrocarbons in the hydrocarbon feed and/or by controlling the ratio of hydrocarbons in the hydrocarbon feed. For example, for a dehydrodimerization of n-heptane and cyclohexane, the ratio of n-heptane and cyclohexane can be adjusted based on a predetermined product composition such as a high yield of bi-cyclohexyl and a low yield of isomers of heptyl-cyclohexane. Accordingly, the average molecular weight of the products can be controlled.

In some embodiments, a catalyst composition loading % can be from about 0.01 wt % to about 50 wt %, such as from about 0.1 wt % to about 5 wt %, such as from about 1 wt % to about 3 wt %, based on a total weight of the hydrocarbon feed and catalyst composition.

In some embodiments, the process to convert the hydrocarbon can be carried out under reaction conditions. The reaction conditions can include a temperature of from about 23° C. to about 200° C., such as from about 25° C. to about 70° C., such as from about 30° C. to about 50° C., alternatively from about 70° C. to about 120° C., such as from about 75° C. to about 90° C. In some embodiments, the reaction conditions include a pressure of from about 0 psig and about 500 psig, such as from about 2 psig to about 100 psig, such as from about 5 psig to about 30 psig, such as from about 10 psig to about 20 psig, such as from about 14 to about 15 psig, alternatively from about 30 psig to about 80 psig, such as from 35 psig to about 40 psig.

Products of the Conversion Process

The processes of present disclosure can provide for various products that include a $C_{2+}$ hydrocarbon, such as a $C_3$-$C_{50}$ hydrocarbon, such as a $C_3$-$C_{12}$ hydrocarbon, such as a $C_6$-$C_{11}$ product, or a $C_{12+}$ distillate product. Products can be cyclic or acyclic, linear or branched. Examples of products include propane, isobutane, n-butane, 2-methyl-butane, pentane, 2,3-dimethyl-butane, 2-methyl-pentane, 3-methyl-pentane, n-hexane, methyl-cyclopentane, 2,4-dimethyl-pentane, 2,2-dimethyl-pentane, 2,2,3-trimethylbutane (triptane), cyclohexene, cyclohexane, n-heptane, other $C_7$ compounds, $C_8$ compounds (acyclic) such as 2,2,4-trimethylpentane (isooctane), 2,2,3,3-tetramethylbutane, $C_8$ compounds (cyclic), $C_8$ compounds (aromatic), $C_9$ compounds (aromatic), $C_{10}$ compounds, $C_{12}$ compounds, and $C_{13+}$ compounds. In some embodiments, a product mixture includes at least one of a $C_6$-$C_{11}$ product(s) or a $C_{12+}$ distillate product(s). The $C_6$-$C_{11}$ products can have a research octane number (RON) of at least 80 and are suitable as blend for high octane gasoline. The RON of a fuel composition can be determined using ASTM D2699-19.

The hydrocarbon product can include an olefin and/or an alkane that is heavier than the hydrocarbon in the hydrocarbon feed. In some embodiments, the hydrocarbon product includes a $C_{2+}$ alkane, such as a $C_2$-$C_{100}$ alkane, such as a $C_3$-$C_{30}$ alkane, such as a $C_6$-$C_{20}$ alkane. In some embodiments, the $C_{2+}$ alkane in the product can be formed by a homocoupling of the $C_{1+}$ alkane of the hydrocarbon feed. In some embodiments, the $C_{2+}$ alkane in the product can be formed by a heterocoupling of at least two different $C_{1+}$ alkanes in the hydrocarbon feed. For example, the hydrocarbon product is a bi-cyclohexyl distillate which is formed by a heterocoupling of n-heptane and cyclohexane.

In some embodiments, the hydrocarbon product can be an alkene, an aromatic compound, or a combination thereof. For example, the hydrocarbon product is 2-heptene which is formed by a dehydrogenation. In some embodiments, the hydrocarbon product can include a cyclic alkane, such as a cyclic alkane having at least two rings.

In some embodiments, a selectivity toward alkanes can be at least about 50 wt %, based on a total weight percent of the product, such as from about 30 wt % to about 95 wt %, such as about 50 wt % to about 95 wt %. Selectivity toward alkanes can be determined by gas chromatography.

In some embodiments, an amount of $C_{3+}$ cyclic alkane converted to a hydrocarbon product can be greater than about 1 wt %, such as from about 5 wt % to about 95 wt %, such as from about 20 wt % to about 75 wt %, such as about 25 wt % to about 70 wt %, such as about 30 wt % to about 40 wt %, alternatively about 40 wt % to about 60 wt %, such as about 40 wt % to about 50 wt %, based on the amount of $C_3$+ cyclic alkane in the hydrocarbon feed as determined by gas chromatography.

In some embodiments, an amount of $C_{1+}$ acyclic alkane converted to a hydrocarbon product can be greater than about 1 wt %, such as from about 5 wt % to about 95 wt %, such as from about 20 wt % to about 75 wt %, such as about 25 wt % to about 70 wt %, based on the amount of $C_{1+}$ acyclic alkane in the hydrocarbon feed as determined by gas chromatography.

In some embodiments, the process can further include separating an unreacted $C_{1+}$ alkane from the product, such as by distillation. In some embodiments, the process further includes separating one or more components of the product based on molecular weight of each components.

Diesel Fuels

Products of the present disclosure, such as products having carbon numbers in the range of from about 5 to about 50, such as from about 12 to about 28, can be used as diesel fuels. The products can be formed from the conversion of a $C_{1+}$ acyclic alkane and/or a $C_{3+}$ cyclic alkane, the diesel fuels having one or more of improved low temperature properties, an improved cloud point, and/or a high cetane number. In at least one embodiment, a diesel fuel is a $C_5$-$C_{50}$ hydrocarbon, such as a $C_{12}$-$C_{28}$ hydrocarbon.

Cetane number (CN) is a measure of ignition quality of diesel fuels. Cetane number is highly dependent on the paraffinicity of molecular structures whether they be straight chain or alkyl attachments to rings. Distillate aromatic content, for example, is inversely proportional to cetane number while a high paraffinic content is directly proportional to a high cetane number. CN for diesel fuels is determined using ASTM D613-18a. Generally, diesel engines operate well with a cetane number of at least about 40. Fuels with a lower cetane number have longer ignition delays, requiring more time for the fuel combustion process to be completed. Hence, higher speed diesel engines operate more effectively with higher cetane number fuels. A product of the present disclosure can be useful as a diesel fuel, as indicated by advantageous cetane numbers. For example, the product(s) formed by methods described herein can have a cetane number of about 30 or greater, such as about 40 or greater, such as about 45 or greater, such as about 48 or greater, such as about 50 or greater, such as about 60 or greater, such as about 70 or greater, such as about 80 or greater, such as about 90 or greater.

Under present conditions, petroleum refineries are increasingly seeking the most cost-effective ways of forming diesel fuel products and improving the quality of such diesel fuel products. The methods described herein can meet this need.

Additional Aspects

The present disclosure provides, among others, the following non-limiting aspects and embodiments, each of which may be considered as optionally including any alternate aspects.

Clause 1. A process for converting a hydrocarbon feed, comprising:
introducing a hydrocarbon feed comprising a alkane to a catalyst composition in a reactor, the catalyst composition comprising a Group 6-Group 15 metal supported on a support; and
irradiating the hydrocarbon feed and the catalyst composition with electromagnetic energy in the reactor at reactor conditions to produce a product comprising a $C_{2+}$ alkane, wherein the $C_{2+}$ alkane of the product is heavier than the alkane in the hydrocarbon feed.

Clause 2. The process of clause 1, wherein the hydrocarbon feed comprises less than about 5 mol % alkenes, based on total mole percent of the hydrocarbon feed as determined by gas chromatography.

Clause 3. The process of any of clauses 1 or 2, wherein the reactor conditions comprises:
a temperature of from about 23° C. to about 200° C.; and
a pressure of from about 0 psig and about 500 psig.

Clause 4. The process of any of clauses 1 to 3, wherein the support has a band gap of about 2 eV to about 4 eV.

Clause 5. The process of any of clauses 1 to 4, wherein the Group 6-Group 15 metal is Fe, Rh, Ru, Ir, Pt, Pd, Ni, Ag, Au, Zn, Ga, Bi, Sn.

Clause 6. The process of any of clauses 1 to 5, wherein the support comprises $TiO_2$, ZnO, $NaNbO_3$, $KNbO_3$, $SrTiO_3$, $PbTiO_3$, $BaCeO_3$, $MoS_2$, $Bi_2O_3$, $BiVO_4$, or a combination thereof.

Clause 7. The process of any of clauses 1 to 6, wherein the hydrocarbon feed comprises methane, ethane, propane, butane, pentane, n-hexane, n-heptane, octane, nonane, decane, undecane, dodecane, cyclopentane, cyclohexane, methylcyclohexane, methylcyclopentane, or a mixture thereof.

Clause 8. The process of any of clauses 1 to 7, wherein the electromagnetic energy has a wavelength greater than about 350 nm.

Clause 9. The process of any of clauses 1 to 8, wherein the electromagnetic energy is ultraviolet A light.

Clause 10. The process of any of clauses 1 to 8, wherein the electromagnetic energy has a wavelength of from about 400 nm to about 600 nm.

Clause 11. The process of any of clauses 1 to 10, wherein the $C_{1+}$ alkane comprises a $C_3$-$C_{12}$ cyclic alkane.

Clause 12. The process of any of clauses 1 to 11, wherein a selectivity toward the $C_3$-$C_{12}$ cyclic alkane is from about 30% to about 95%, based on total weight percent of the product as determined by gas chromatography.

Clause 13. The process of any of clauses 1 to 12, wherein the $C_{1+}$ alkane comprises a $C_2$-$C_{12}$ acyclic alkane.

Clause 14. The process of clause 13, wherein the $C_2$-$C_{12}$ acyclic alkane of the hydrocarbon feed comprises a linear alkane and a branched alkane.

Clause 15. The process of any of clauses 1 to 14, wherein the product comprises alkenes.

Clause 16. The process of any of clauses 1 to 15, wherein the product comprises a cyclic alkane, the cyclic alkane comprising at least two rings as determined by gas chromatography.

Clause 17. The process of any of clauses 1 to 16, wherein the reactor conditions comprise:
a temperature of from about 23° C. to about 70° C.; and
a pressure of from about 0 psig and about 50 psig.

Clause 18. The process of any of clauses 1 to 17, wherein the hydrocarbon feed and the catalyst composition is irradiated for about 24 hours or less.

Clause 19. The process of any of clauses 1 to 18, wherein the hydrocarbon feed is free or substantially free of functionalized hydrocarbons.

Clause 20. The process of any of clauses 1 to 19, wherein the hydrocarbon feed includes from about 10 to about 1000 ppm $H_2O$.

Clause 21. The process of any of clauses 1 to 20, wherein the $C_{2+}$ alkane in the product are formed by a homocoupling of the alkane of the hydrocarbon feed.

Clause 22. The process of any of clauses 1 to 21, wherein the hydrocarbon feed comprises at least two different $C_{1+}$ alkanes, and wherein the $C_{2+}$ alkane in the product is formed by a heterocoupling of at least two different alkanes in the hydrocarbon feed.

Clause 23. The process of any of clauses 1 to 22, wherein the catalyst composition has a total surface area of from about 5 m$^2$/g to about 500 m$^2$/g, as determined by BET method.

Clause 24. The process of any of clauses 1 to 23, wherein the catalyst composition is free or substantially free of one or more group 12 metals.

Clause 25. The process of any of clauses 1 to 24, wherein the C$_{2+}$ alkane comprises a C$_6$-C$_{20}$ alkane.

Clause 26. The process of any of clauses 1 to 25, wherein the C$_{1+}$ alkane comprises a C$_2$-C$_{10}$ alkane.

Clause 27. The process of any of clauses 1 to 26, further comprising separating an unreacted C$_{1+}$ alkane from the product.

Clause 28. The process of any of clauses 1 to 27, further comprising separating one or more components of the product based on molecular weight of each component.

Clause 29. The process of any of clauses 1 to 28, wherein the product comprises C$_6$-C$_{11}$ alkane with a research octane number (RON) of at least about 80, according to ASTM D2699-19.

Clause 30. The process of any of clauses 1 to 29, wherein the product comprises C$_{12}$-C$_{25}$ alkane with a cetane number (CN) of at least about 50, according to ASTM D613-18a.

Clause 31. A process for converting a hydrocarbon feed, comprising:
introducing a hydrocarbon feed comprising a alkane to a catalyst composition in a reactor, the catalyst composition comprising a Group 6-Group 15 metal supported on a support; and
irradiating the hydrocarbon feed and the catalyst composition with electromagnetic energy in the reactor at reactor conditions to produce a product comprising a C$_{2+}$ alkene.

Clause 32. A process for converting a hydrocarbon feed, comprising:
introducing a hydrocarbon feed comprising a C$_2$-C$_{12}$ alkane to catalyst composition in a reactor, the catalyst composition comprising a Group 10 metal supported on an oxide support; and
irradiating the hydrocarbon feed and the catalyst composition with UV-A radiation in the reactor at reactor conditions to produce a product comprising a C$_4$-C$_{24}$ alkane, wherein the C$_{4+}$ alkane of the product is heavier than the C$_4$-C$_{24}$ alkane in the hydrocarbon feed.

Clause 33. The process of clause 32, wherein the reactor conditions comprise:
a temperature of from about 23° C. to about 40° C.; and
a pressure of from about 14 psig and about 16 psig.

Clause 34. The process of any of clauses 32 and 33, wherein the hydrocarbon feed further comprises a C$_3$-C$_{12}$ cyclic alkane, wherein the C$_2$-C$_{12}$ alkane is an acyclic alkane, and/or wherein the C$_4$-C$_{24}$ alkane in the product is formed by a heterocoupling of at least of the C$_3$-C$_{12}$ cyclic alkane in the hydrocarbon feed and the C$_2$-C$_{12}$ acyclic alkane in the hydrocarbon feed.

EXAMPLES

The following examples are presented for illustrative purposes and should not be construed as limiting any concepts to any particular embodiment of the present disclosure.

The various types of hydrocarbons formed from the following examples can be determined using Gas Chromatography-Mass Spectrometry.

Gas Chromatography (GC): For the conversion process, the products were analyzed using a GC (Agilent 6890 Plus) with an FID detector and a HP-PONA column (50 m length×0.2 mm diameter×0.5 µm film thickness). The GC conditions were the following: Injector: 225° C.; 0.5 µL injection volume, 100/1 split ratio. Detector: 250° C. Oven: 35° C. (10 min), 2.5° C./min to 135° C., 10° C./min to 320° C. (6.5 min). Gas chromatography-mass spectrometry (GC/MS) is used to identify the reaction products. The GC/MS is performed on an Agilent 6890 GC equipped with an Agilent 5975 MSD detector. The GC column and oven conditions are identical to the GC described above.

The following examples provide comparative data and example embodiments of the present disclosure. In particular, example 1 is a comparative process of n-heptane irradiated in the presence of TiO$_2$ without a metal nanoparticle; example 2 is an embodiment of the present disclosure of n-heptane irradiated in the presence of Pt/TiO$_2$; example 3 is an embodiment of the present disclosure using a cycloalkane as a starting material; and example 4 is an embodiment of the present disclosure using a mixture of cyclic alkane and acyclic alkane as a starting material.

Example 1. Irradiation of n-heptane on TiO$_2$

The hydrocarbon feed, 20-mL of anhydrous n-heptane, was introduced into a 0.5" i.d. quartz reactor tube inside a dry-box along with 0.5 g of TiO$_2$ photocatalyst (Aeroxide P25, purchased from Sigma-Aldrich). The tube was placed in the Rayonet photoreactor (Branford, Conn.; model RPR-100) and irradiated using 350 nm (UV-A) lamps at 23° C. and 1 atmosphere (14.7 psig) for 22 hours. The liquid was sampled and analyzed by GC and confirmed with GC/MS. No reaction was detected by gas chromatography. The GC trace is shown in FIG. 1 as described below.

Example 2. Photocatalytic Dehydrodimerization of n-heptane

The hydrocarbon feed, 20-mL of anhydrous n-heptane, was introduced into a 0.5" i.d. quartz reactor tube inside a dry-box along with 0.5 g of Pt/TiO$_2$ photocatalyst (1 wt % Pt, purchased from Strem Chemical). The tube was placed in the Rayonet photoreactor (RPR-100) and irradiated using 350 nm (UV-A) lamps at 23° C. and 1 atmosphere (0 psig) for 21 hours. The liquid was sampled and analyzed by GC. Formation of C14 alkanes (105) was observed and confirmed by GC/MS; total yield to C14 alkanes was 1.3 wt % based on the total amount of feed. Trace amount of olefins (heptenes) were also observed, with yield less than about 0.1%.

The GC/MS trace of the sampled liquid is shown in FIG. 1. In particular, FIG. 1 provides the GC/MS trace for three samples including a starting material n-heptane (101), a comparative, n-heptane irradiated with UV-A light in the presence of TiO$_2$ (102) detailed in Example 1, and a non-limiting example of the present disclosure, n-heptane irradiated with UV-A light in the presence of Pt/TiO$_2$ (103), detailed in Example 2. The GC trace for each sample showed peaks for n-heptane (104) between 10 mins to 20 mins; however, n-heptane irradiated with UV-A in the presence of TiO$_2$ (102) did not show any evidence of C14 alkane formation. Formation of C14 alkanes (105) was observed for the example of the present disclosure and confirmed by GC/MS.

Example 3. Photocatalytic Dehydrodimerization of Cyclohexane

Figure 2:
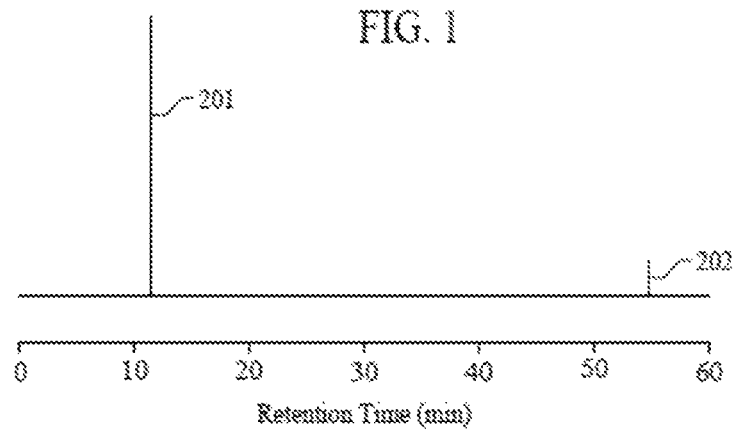
FIG. 2 depicts a GC trace of an example cyclohexane irradiated with UV-A light in the presence of $Pt/TiO_2$, according to at least one embodiment of the present disclosure.

The hydrocarbon feed, 20-mL of anhydrous cyclohexane, was introduced into a 0.5" i.d. quartz reactor tube inside a dry-box along with 0.48 g of Pt/TiO$_2$ photocatalyst (1 wt % Pt, purchased from Strem Chemical). The tube was placed in the Rayonet photoreactor (RPR-100) and irradiated using 350 nm (UV-A) lamps at 23° C. and 1 atmosphere (0 psig) for 19 hours. The liquid was sampled and analyzed by GC and GC/MS. The GC trace of the sample is shown in FIG. 2 which showed the presence of cyclohexane (201) and formation of bi-cyclohexyl (202) which was confirmed by GC/MS; yield to bi-cyclohexyl was about 0.4 wt % based on the amount of cyclohexane used in the reaction.

Figure 3:
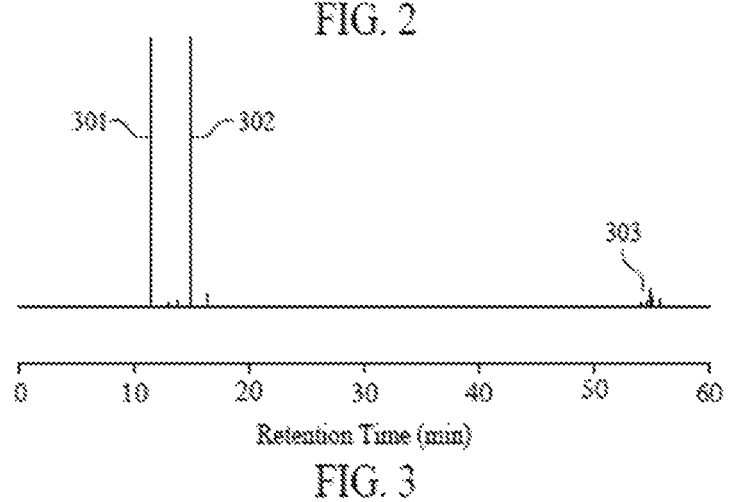
FIG. 3 depicts a GC trace of an example cyclohexane and n-heptane mixture irradiated with UV-A light in the presence of $Pt/TiO_2$, according to at least one embodiment of the present disclosure.

Example 4. Photocatalytic Dehydrodimerization of n-Heptane and Cyclohexane Mixture The hydrocarbon feed, 20-mL of anhydrous cyclohexane and n-heptane mixture (1/1 vol/vol), was introduced into a 0.5" i.d. quartz reactor tube inside a dry-box along with 0.25 g of Pt/TiO$_2$ photocatalyst (1 wt % Pt, purchased from Strem Chemical). The tube was placed in the Rayonet photoreactor (RPR-100) and irradiated using 350 nm (UV-A) lamps at 23° C. and 1 atmosphere (0 psig) for 20 hours. The liquid was sampled and analyzed by GC and GC/MS. The GC trace of the sample is shown in FIG. 3 which showed the presence of unreacted cyclohexane (301) and n-heptane (302). The GC trace also shows evidence of the formation of bi-cyclohexyl as well as four isomers of heptyl-cyclohexane (1-, 2-, 3-, and 4-cyclohexylheptane) (303) which were confirmed by GC/MS; total yield was about 0.3 wt % based on the amount of feed used.

Example 5a. Preparation of TiO$_2$

TiO$_2$ can be prepared from dissolving a titanium ore in sulphuric acid, removing iron from the mixture, hydrolyzing the iron-reduced mixture to produce a hydrated titanium dioxide, and heating the hydrated titanium dioxide to produce solid titanium dioxide as described in Barben Analytical "Application Note Titanium Dioxide-Sulfate Process," which is incorporated herein by reference in its entirety. In some embodiments, the TiO$_2$ can be prepared from combining titanium ore with coke (C$^+$) and chlorine gas at elevated temperature to produce a titanium tetrachloride, removing the chlorine gas by oxidation to form titanium dioxide. In some embodiments, the titanium ore can be selected from a group consisting of ilmenite, rutile, leucoxene, titanium slag, and a combination thereof.

Example 5b. Preparation of M/TiO$_2$

In some examples, the catalyst composition (semiconductor component and metal nanoparticle component) can be prepared by thermal impregnation, chemical reduction, photodeposition, and/or using cold plasma techniques. For example, and in some embodiments, Pt/TiO$_2$ can be prepared by thermal impregnation, chemical reduction, photodeposition, or using cold plasma techniques as described in Di, Lanbo et al. "A facile method for preparing Pt/TiO$_2$ photocatalyst with enhanced activity using dielectric barrier discharge." Catalysis Today, 211 (2013) 109-113, which is incorporated herein by reference in its entirety.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

What is claimed is:

1. A process for converting a hydrocarbon feed, comprising:
introducing a hydrocarbon feed comprising a C$_2$-C$_{12}$ alkane to a catalyst composition in a reactor, the catalyst composition comprising a Group 10 metal supported on a semiconductor component, the semiconductor component comprises an oxide and has a band gap between 2.0 eV and 4.0 eV; and
irradiating the hydrocarbon feed and the catalyst composition with UV-A radiation in the reactor at a temperature of 23° C. to 200° C. and a pressure between 0 psig and 500 psig to produce a product comprising a C$_4$-C$_{24}$ alkane, wherein the C$_4$-C$_{24}$ alkane of the product is heavier than the C$_4$-C$_{24}$ alkane in the hydrocarbon feed.

2. The process of claim 1, wherein the hydrocarbon feed comprises less than about 5 mol % alkenes, based on total mole percent of the hydrocarbon feed as determined by gas chromatography.

3. The process of claim 1, wherein the reactor temperature is from about 23° C. to about 70° C. and pressure is from about 0 psig and about 500 psig.

4. The process of claim 1, wherein the product comprises alkenes.

5. The process of claim 1, wherein the product comprises a cyclic alkane, the cyclic alkane comprising at least two rings as determined by gas chromatography.

6. The process of claim 1, wherein the hydrocarbon feed and the catalyst composition is irradiated for about 24 hours or less.

7. The process of claim 1, wherein the hydrocarbon feed is free or substantially free of functionalized hydrocarbons.

8. The process of claim 1, wherein the hydrocarbon feed includes from about 10 to about 1000 ppm H$_2$O.

9. The process of claim 1, wherein the catalyst composition is free or substantially free of one or more group 12 metals.

10. The process of claim 1, further comprising separating one or more components of the product based on molecular weight of each component.

11. The process of claim 1, wherein the product comprises $C_6$-$C_{11}$ alkane with a research octane number (RON) of at least about 80, according to ASTM D2699-19.

12. The process of claim 1, wherein the hydrocarbon feed further comprises a $C_3$-$C_{12}$ cyclic alkane, wherein the $C_2$-$C_{12}$ alkane is an acyclic alkane, and wherein the $C_4$-$C_{24}$ alkane in the product is formed by a heterocoupling of at least of the $C_3$-$C_{12}$ cyclic alkane in the hydrocarbon feed and the $C_2$-$C_{12}$ acyclic alkane in the hydrocarbon feed.

* * * * *